United States Patent [19]

Kurosaki et al.

[11] Patent Number: 5,658,532
[45] Date of Patent: Aug. 19, 1997

[54] CUVETTE AND CUVETTE-TRANSPORTING APPARATUS

[75] Inventors: Tsuyoshi Kurosaki; Masayuki Nakagawa, both of Hyogo, Japan

[73] Assignee: TOA Medical Electronics Co., Ltd., Hyogo, Japan

[21] Appl. No.: 535,519

[22] Filed: Sep. 28, 1995

[30] Foreign Application Priority Data

Sep. 30, 1994 [JP] Japan .................... 6-274173

[51] Int. Cl.$^6$ .................... G01N 35/04; G01N 21/03
[52] U.S. Cl. .................... 422/64; 422/63; 422/65; 422/102; 422/104; 436/43; 436/47; 436/48; 436/164; 436/165; 215/371; 215/383; 215/384; 220/604; 220/670; 220/675
[58] Field of Search .................... 422/63, 64, 65, 422/67, 102, 104; 436/43, 47, 48, 164, 165; 215/371, 382, 383, 384; 220/604, 670, 675; D24/224

[56] References Cited

U.S. PATENT DOCUMENTS

| | | | |
|---|---|---|---|
| D. 222,352. | 10/1971 | Ferro et al. | D24/224 |
| D. 330,428 | 10/1992 | Lewis et al. | D24/224 |
| 3,627,432 | 12/1971 | Bergmann | 422/102 |
| 3,788,815 | 1/1974 | Rohrbaugh | 422/102 |
| 3,998,594 | 12/1976 | Home | 422/102 |
| 4,357,301 | 11/1982 | Cassaday et al. | 422/64 |
| 4,427,634 | 1/1984 | Truglio | 422/99 |
| 4,628,036 | 12/1986 | Scheepens et al. | 436/520 |
| 4,634,576 | 1/1987 | Galle et al. | 422/102 |
| 4,659,550 | 4/1987 | Schildknecht | 422/73 |
| 4,974,460 | 12/1990 | Baxter | 73/864.91 |
| 5,098,661 | 3/1992 | Froehlich et al. | 422/102 |
| 5,310,527 | 5/1994 | Romanauskas et al. | 422/102 |
| 5,352,413 | 10/1994 | Kratzer et al. | 422/100 |
| 5,434,083 | 7/1995 | Mitsumaki et al. | 436/48 |
| 5,437,841 | 8/1995 | Balmer | 422/102 |
| 5,452,881 | 9/1995 | Hayashi | 266/79 |
| 5,462,715 | 10/1995 | Koch et al. | 422/64 |
| 5,472,669 | 12/1995 | Miki et al. | 422/63 |
| 5,525,298 | 6/1996 | Anami | 422/63 |

FOREIGN PATENT DOCUMENTS

| | | |
|---|---|---|
| 3-25157 | 3/1991 | Japan . |
| 7-43523 | 8/1995 | Japan . |

*Primary Examiner*—Long V. Le

[57] ABSTRACT

A cuvette, to be used for measuring the properties of liquid contained therein by applying a measuring beam of light from a direction intersecting the vertical axis of the cuvette, includes a rectangular or square-outlined portion on the top thereof as viewed in a horizontal cross section, a cylindrical portion below the top portion, and a lower rectangular or square portion provided vertically below the cylindrical portion and having four sides parallel to these of the top rectangular portion, respectively. Thus, the cuvette does not unfavorably rotate when measuring the absorption of light transmitted therethrough. Further, an apparatus for transporting the aforementioned transparent cuvette, accurately controls the position of the cuvette during transportation so that a flat surface thereof can be irradiated with a measuring beam of light.

13 Claims, 6 Drawing Sheets

FIG. 7

CUVETTE AND CUVETTE-TRANSPORTING APPARATUS

BACKGROUND OF THE INVENTION

1. Field of the Invention

The present invention relates to a cuvette for containing a liquid to be measured such as a specimen and a reagent for analyzing the constituents of plasma, urine, or others. Further, it relates to a cuvette-transporting apparatus for transporting the cuvette while controlling its position.

2. Description of Related Art

Conventional cuvettes and cuvette-transporting apparatuses are disclosed in Japanese Unexamined Utility Model Publication No. Hei 3(1991)-25157 and will hereinafter be explained with reference to FIGS. 6 and 7 which are a plan view and a vertical sectional view, respectively.

As shown in these drawings, a cuvette 1 is only of a cylindrical shape like a test tube and is provided with a flange 2 on the top thereof.

The cuvette-transporting apparatus comprises a chute 3 for transferring the cuvettes 1 with their heads (the top portion of the cuvette 1 which is open to receive the liquid) arranged in a line, and a positioning unit 4 for separating the cuvettes 1 from each other and for slightly lifting the cuvettes 1 up.

The positioning unit 4 is provided with a cylindrical space 5 having a rotator 8 rotatably inserted therein which comprises two circular boards 8 and 7 disposed parallel to each other.

Each of the circular boards 6 and 7 is provided with three arc-like notches 9, each notch being equally spaced on each circular board and located at upper and lower common positions. The notches 9 are formed so as to have the diameter thereof larger than the diameter of the body of the cuvette 1 and smaller than the diameter of the flange 2.

The positioning unit 4 has a motor 10 provided on the lower side, with a rotating shaft 11 of the motor 10 fixed into the rotator 8 at the center thereof, such that the motor 10 rotates the rotator 8 clockwise as shown in FIG. 8. Thus, the rotation of the motor 10 allows the cuvettes 1, together with the circular boards 6 and 7, to partially rotate around the center of the rotator 8.

In an outlet for the cuvettes 1 is provided a bottom guide 12 inclined such that the cuvettes 1 travel upward onto-the top of the guide. Further, lateral guides 13 and 14 are provided for slidingly contacting the lateral sides of the cuvettes 1 such that the lower circular board 6 is sandwiched therebetween.

Reference numeral 15 denotes a microswitch, for detecting the presence or absence of the cuvette 1, and numeral 16 denotes its actuator. The cuvettes 1, thus sequentially transferred in a line through the chute 3, are allowed to separate from each other and are individually inserted into the notches 9 of the circular boards 6 and 7 in a horizontal direction. In accordance with the rotation of the rotator 8, the cuvettes 1, together with the circular boards 6 and 7, are allowed to partially rotate around the center of the rotator 8.

Figure 6:
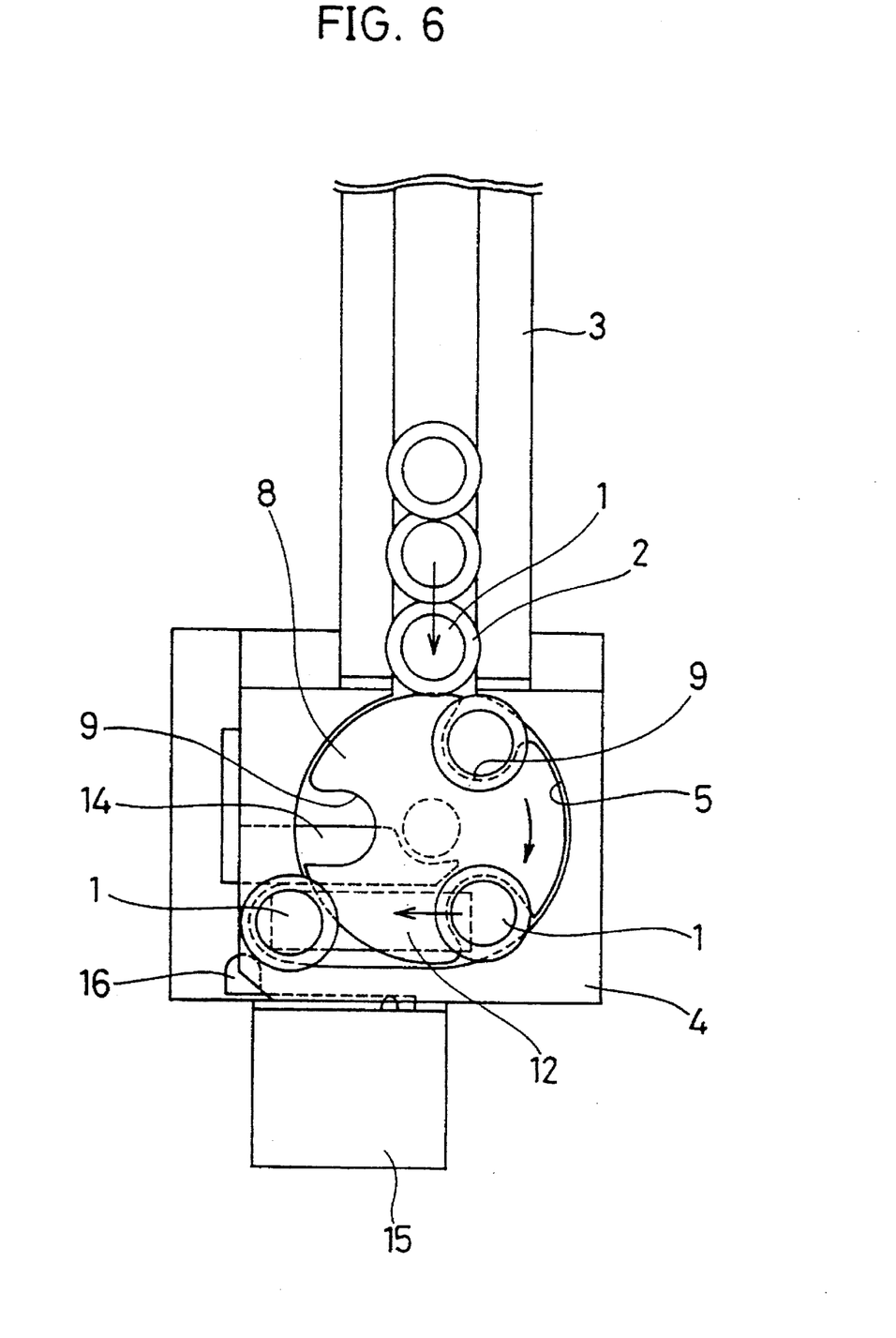
FIG. 6 is a plan view of a conventional cuvette-transporting apparatus.

After arriving at the foot of the bottom guide 12, the cuvette 1 travels upward with the outer bottom portion sliding on the bottom guide 12 to reach the top thereof and simultaneously is guided to the left by the lateral guides 13 and 14 (see FIG. 6). Thereafter, it is then detached from the notches 9 of the circular boards 6 and 7.

The cuvette 1, thus detached from the rotator 8, is resiliently held by a chucking finger with an arc-like inside to be transferred to a predetermined location.

The conventional cuvette 1 as described above has been, since it freely rotates, disadvantageous in measuring the properties of a liquid contained in the cuvette 1 by applying a measuring beam of light from a direction intersecting the vertical axis of the cuvette 1.

In order to precisely measure the absorption of transmitted light passing through the cuvette 1, a flat-surface is required to be formed on the cuvette 1 for applying the measuring beam of light. Such a flat surface, however, may not necessarily be irradiated with the measuring beam of light due to the rotation occurring during the transfer of the cuvette 1. Therefore the formation of the flat surface becomes useless.

SUMMARY OF THE INVENTION

The present invention has been made in view of the above problems in the prior art. Thus, a first object of the present invention is to achieve a cuvette which does not unfavorably rotate. A next object is to achieve a cuvette-transporting apparatus which controls the position of the cuvette during the transportation to irradiate a flat surface thereof with the measuring beam of light.

In one aspect, the present invention attains the aforementioned and other objects by providing a cuvette to be used for measuring the properties of a liquid contained therein by applying a measuring beam of light from a direction intersecting the vertical axis of the cuvette having a rectangular (two pairs of parallel sides, each pair of sides being of a different length) or square-outlined (two pairs of parallel sides, each pair of sides being of the same length) portion on the top thereof as viewed in a horizontal cross section, a cylindrical portion below the top portion, and a lower rectangular or square portion vertically below the cylindrical portion and having four sides, each respectively parallel to at least one of the four sides of the top rectangular or square portion.

The liquid to be contained in the cuvette in accordance with the present invention is a specimen such as plasma and urine, to which a reagent may or may not be added.

The measuring beam of light to be applied to the cuvette can be visible light or infrared light, and the transmitted light and/or scattered light thereof are measured by a light detector to give optical properties for the analysis of the constituents of the specimen.

The cuvette of the invention is preferably molded out of resin from the viewpoint of mass production. The cuvette is usually made transparent or light-pervious enough for a measuring beam of light to pass through, or a portion thereof may be made transparent or light-pervious enough for the measuring beam of light to pass through.

In another aspect, the present invention attains the aforementioned and other objects by providing a cuvette transporting apparatus for transporting a cuvette which has a rectangular or square-outlined portion (of two pairs of parallel sides) on the top thereof as viewed in a horizontal cross section, and a cylindrical portion below the top portion. The cuvette-transporting apparatus comprises a pair of horizontally extending straight upper gripping arms for gripping the top rectangular or square portion of the cuvette, and a pair of horizontally extending lower gripping arms internally curved for gripping the cylindrical portion of the cuvette.

In still another aspect, the present invention attains the aforementioned and other objects by providing a cuvette-transporting apparatus for transporting a cuvette which has a rectangular or square-outlined (of two pairs of parallel sides) portion on at least a part thereof as viewed in a horizontal cross section and is used for measuring the properties of a liquid by applying a measuring beam of light from a direction intersecting the vertical axis of the cuvette. The cuvette-transporting apparatus comprises a cuvette-holding means for loose-fittingly holding the cuvette and rotating it around a predetermined center, and a position-controlling means for controlling the position of the cuvette by slidingly contacting the rectangular or square portion of the cuvette during the rotation.

These and other objects of the present invention will become more readily apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1($a$) is a perspective view illustrating the external appearance of a first cuvette-transporting apparatus in accordance with the present invention and FIG. 1($b$) is a perspective view illustrating the external appearance of a second cuvette-transporting apparatus in accordance with the present invention.

DESCRIPTION OF THE PREFERRED EMBODIMENTS

The present invention will hereinafter be described in detail by way of embodiments thereof shown in the attached drawings These embodiments are not intended to limit the scope of the present invention.

Figures 1A, 1B:
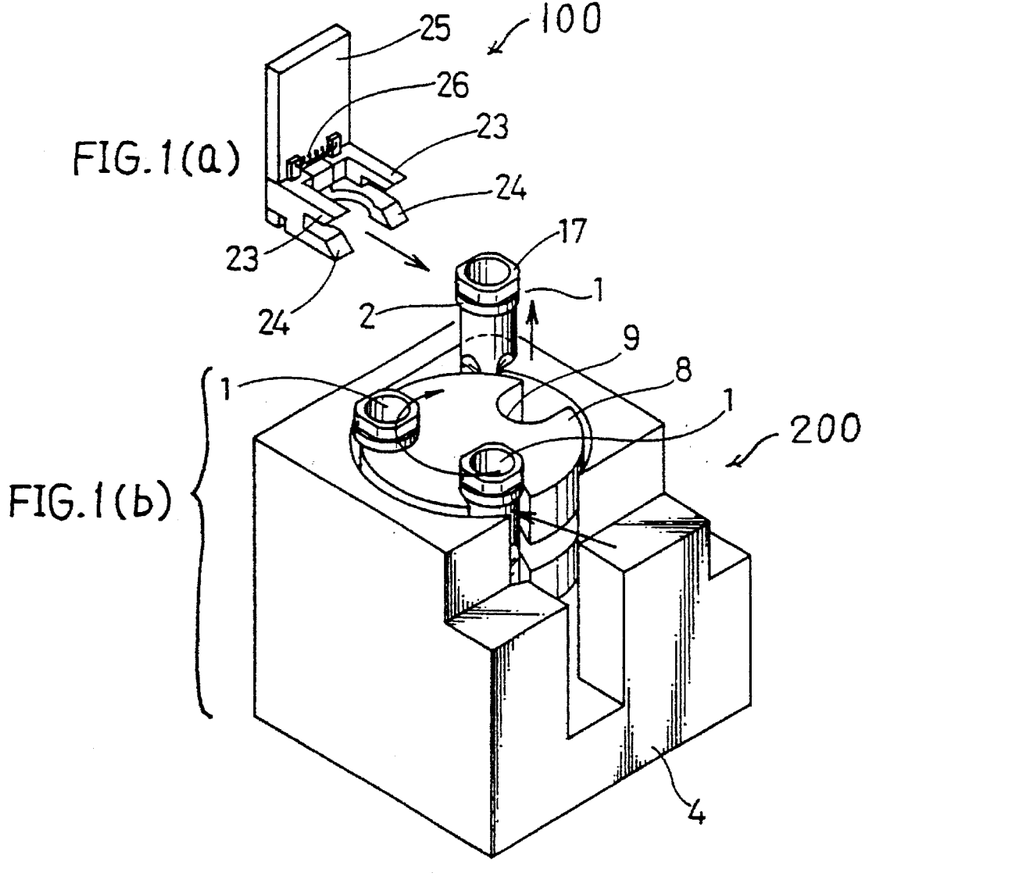
Figure 2:
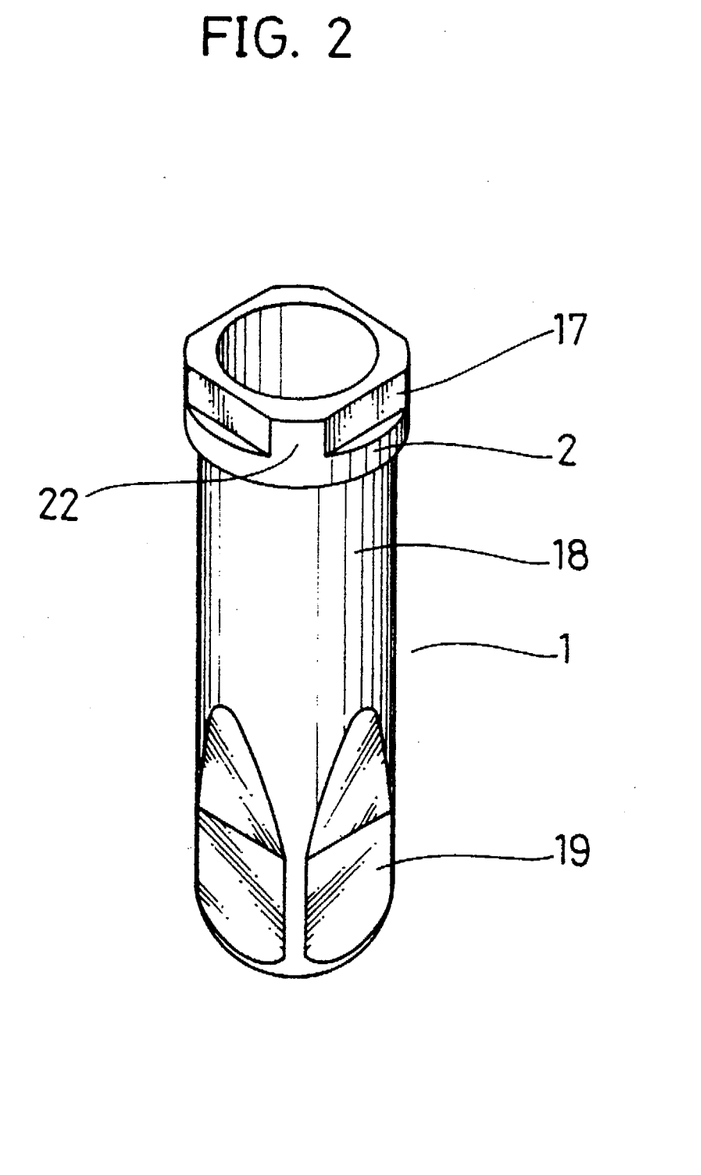
FIG. 2 is a perspective view illustrating the external appearance of the cuvette in accordance with the present invention.
Figure 3:
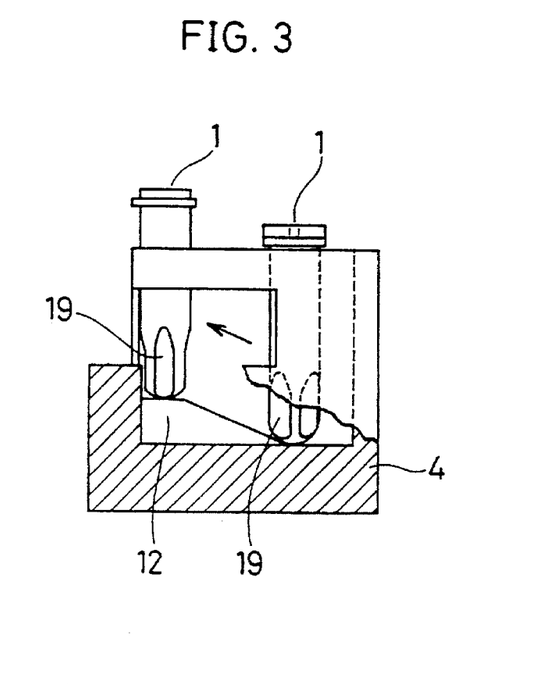
FIG. 3 is a partial sectional side view illustrating the second cuvette-transporting apparatus.
Figure 4:
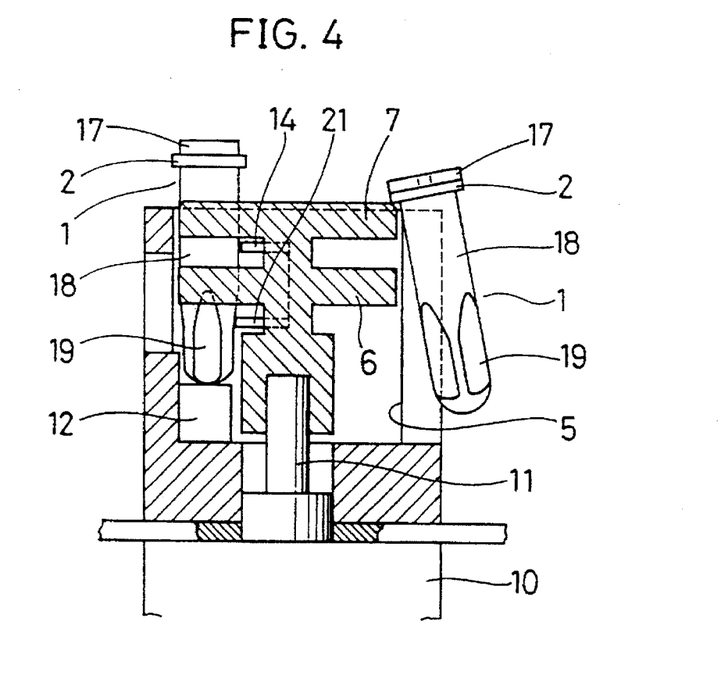
FIG. 4 is a partial sectional front view illustrating the second cuvette-transporting apparatus.

FIGS. 1 to 5 show examples of the present invention. A first cuvette-transporting apparatus 100 and a second cuvette-transporting apparatus 200 are shown in FIG. 1($a$) and FIG. 1($b$), respectively. A transparent cuvette 1 in accordance with the present invention is shown in FIG. 2. FIG. 3 is a partial sectional side view illustrating the second cuvette-transporting apparatus 200. FIG. 4 is a partial sectional front view illustrating the second cuvette-transporting apparatus 200. FIG. 8 is a perspective exploded view of the second cuvette-transporting apparatus 200.

Figure 7:
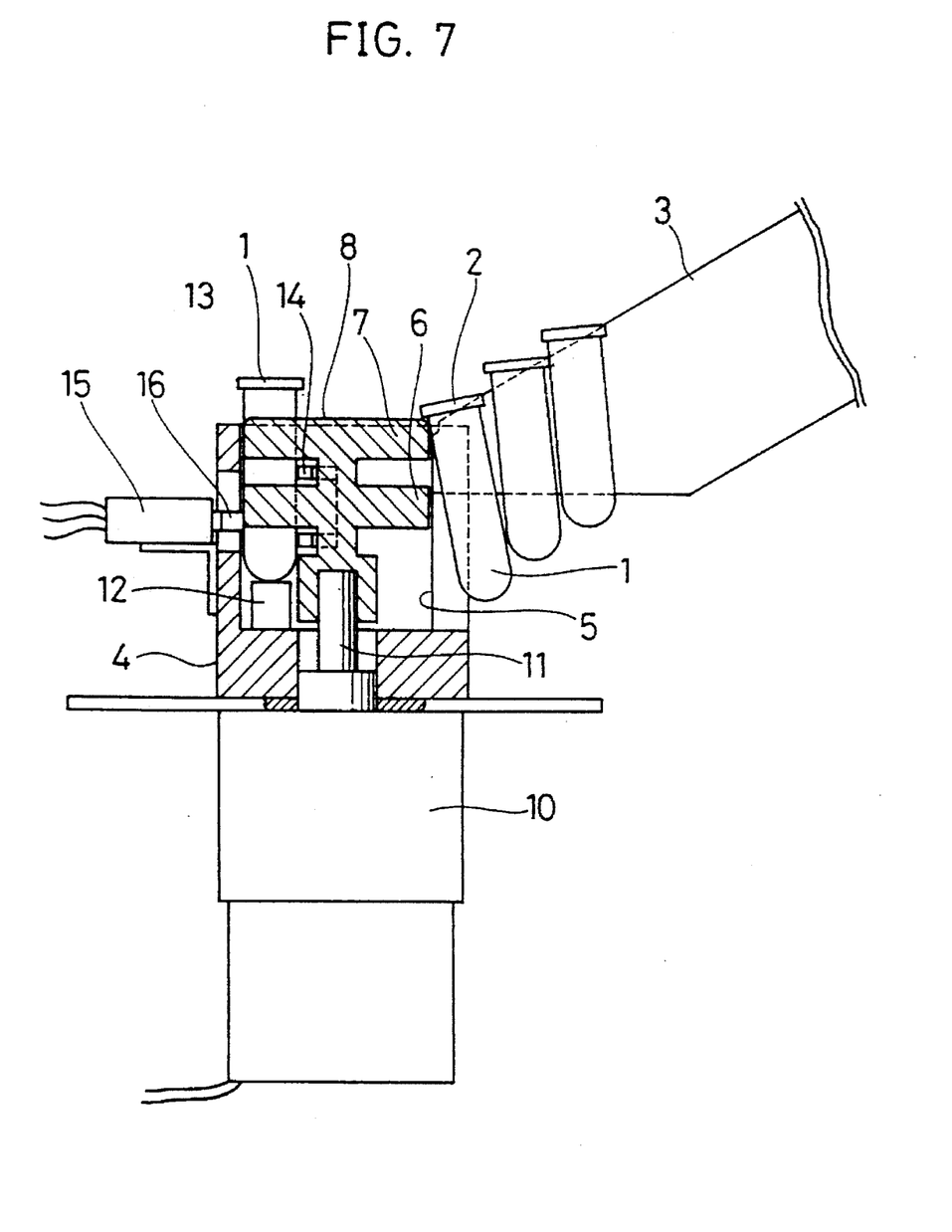
FIG. 7 is a vertical sectional view of the conventional cuvette-transporting apparatus.

The identical reference numerals in FIGS. 1 to 5 denote identical parts corresponding to the ones shown in prior art FIGS. 6 and 7.

Referring to FIG. 2, the cuvette 1 has a rectangular (including two pairs of parallel sides, one pair of sides being of a first length and the other pair of sides being of a second length, different from the first length) or square-outlined (including two pairs of parallel sides, all sides being of a common length) portion 17 on the top thereof as viewed in a horizontal cross section. Vertically, below the top rectangular or square portion 17, is provided a round flange 2. Immediately below the flange 2, there extends a cylindrical portion 18 by a predetermined length (approximately 1 cm). Vertically, below the cylindrical portion 18, is provided a lower rectangular or square portion 19 which has four external sides, each respectively parallel to at least one of the four sides of the rectangular or square portion 17, as viewed in a horizontal cross section.

The cuvette 1 is internally cylindrical from the top rectangular or square portion 17 to the cylindrical portion 18, and the lower rectangular portion 19 has inner rectangular surfaces (including four sides) each respectively parallel to a corresponding outer external rectangular surfaces or sides thereof. Thus, internally, the cuvette 1 is cylindrical on the upper side and prismatic on the lower side. The inside at the top rectangular or square portion 17 may be rectangular or square, as can the outside. In that case, the top rectangular or square portion 17 has a uniform thickness, thereby inhibiting possible distortion during the formation of the cuvette 1 out of resin, for example.

Figure 5:
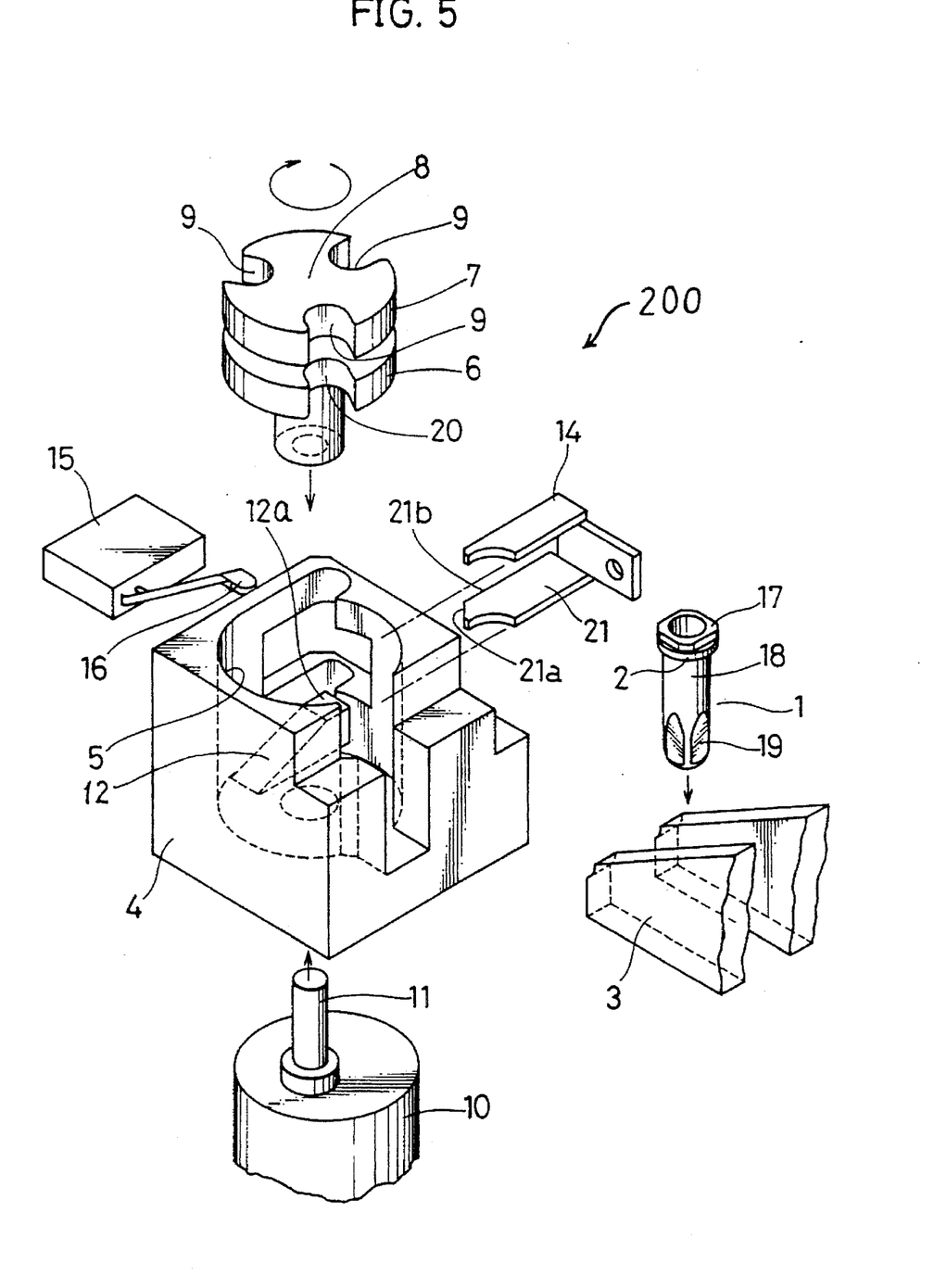
FIG. 5 is a perspective exploded view of the second cuvette-transporting apparatus.

FIG. 5 illustrates the second cuvette-transporting apparatus 200 including a chute 3 for transferring the cuvettes 1 with their heads arranged in a line, and a positioning unit 4 for separating the cuvettes 1 from each other and slightly lifting the cuvettes 1 up.

The positioning unit 4 is provided with a cylindrical space 5 having a rotator 8 rotatably inserted therein which comprises two circular boards 8 and 7 disposed parallel to each other.

Each of the circular boards 6 and 7 is circumferentially provided with three arc-like notches 20 and 9, respectively, each notch being equally spaced on each circular board and located at upper and lower common positions. The notches 20 and 9 are formed so as to have the diameter thereof slightly larger than the diameter of the cylindrical portion 18 of the cuvette 1 and slightly smaller than the diameter of the flange 2. The number of arc-like notches is not limited to three, and may be more or less than three.

The positioning unit 4 has a motor 10 provided on the lower side, with a rotating shaft 11 fixed into the rotator 8 at the center thereof, such that the motor 10 rotates the rotator 8 clockwise as shown in FIG. 6. Thus, the cuvettes 1 slidingly fall while being sustained on the chute 3 to be supplied further, the cuvettes 1 are horizontally and loose-fittingly inserted into the notches 20 and 9 by the rotation of the motor 10, and partially rotate together with the rotator 8 around the axis of the rotator 8.

In an outlet for the cuvettes 1 is provided a bottom guide 12 inclined such that the cuvettes 1 travel upward onto the top of the guide. Further, lateral guides 14 and 21 are also provided for slidingly contacting the lateral sides of the cuvettes 1 such that the lower circular board 8 is sandwiched therebetween.

Of the lateral guides 14 and 21, the lower guide 21 differs in configuration from the lateral guide 13 of the prior art. As shown in FIGS. 4 and 5, the lower guide 21 is wider and longer than lateral guide 13, having a slidingly contacting portion extending slightly more inside a passage through which the cuvettes 1 pass (closer to the cuvettes 1), such that the slidingly contacting portion of the lower guide 21 slidingly contacts the lower rectangular portion 19 of the cuvette 1.

As shown in FIG. 5, the lower guide 21 has a tapered section 21$a$ for guiding the cuvettes 1.

Reference numeral 15 denotes a microswitch for detecting the presence or absence of the cuvette 1 and numeral 16 denotes its actuator.

The cuvettes 1, thus sequentially transferred in a line through the chute 3, are allowed to separate from each other and are individually inserted into the notches 20 and 9 of the circular boards 6 and 7 in a horizontal direction. In accordance with the rotation of the rotator 8, the cuvettes 1, together with the circular boards 6 and 7, are allowed to partially rotate around the center of the rotator 8.

When the cuvette 1 comes into contact with the lateral guides 14 and 21, the lower rectangular portion 19 of the cuvette 1 slidingly contact is the tapered section 21a of the lower guide 21. Further, since the cuvette 1 is loosely fitted in the notches 9 and 20, the cuvette 1 is allowed to suitably rotate within the notches 9 and 20 until it becomes stable with the lower rectangular portion 19 abutting against the linear portion 21b of the lower guide 21.

When the cuvette 1 comes into contact with the lateral guides 14 and 21, the cuvette 1 also contacts the bottom guide 12 at the bottom thereof and travels upward as it slides on the bottom guide 12 to the top portion 12a of the bottom guide 12.

Thus, the cuvette 1 is guided in a controlled state such that one of the surfaces of the lower rectangular portion 19 is parallel to the linear portion 21b of the lateral guide 21 (serving as a position-controlling device, for example), and is then detached from the notches 9 and 20 in the circular boards 6 and 7.

A first cuvette-transporting apparatus 100 will now be detailed with reference to FIG. 1 (a).

A driving body 25 fixed to a driving apparatus (not shown) is provided with a chucking finger 27 comprising a pair of horizontally extending straight upper gripping arms 23, 23 for horizontally gripping the top rectangular or square portion 17 of the cuvette 1; and a pair of horizontally extending lower gripping arms 24, 24 internally curved for horizontally gripping the cylindrical portion 18 of the cuvette 1.

One upper gripping arm 23 is formed integrally with one lower gripping arm 24 and the other upper gripping arm 23 is formed integrally with the other lower gripping are 24, with a tensile coiled spring 26 therebetween. Thus, one upper gripping arm 23 and one lower gripping arm 24 are resiliently pressed against the other upper gripping arm 23 and the other lower gripping arm 24, respectively.

The upper gripping arms 28, 23 are spaced apart from the lower gripping arms 24, 24 slightly farther than the thickness of the flange 2. The cuvette 1 is held in such a manner that the upper gripping arms 23, 23 horizontally hold the top rectangular or square portion 17 and the lower gripping arms 24, 24 horizontally hold the cylindrical portion 18 below the flange 2, whereby the flange 2 is sandwiched between the upper gripping arms 2S, 23 and the lower gripping arms 24, 24.

When the chucking finger 27, comprising the pair of upper gripping arms 23, 23 and the pair of lower gripping arms 24, 24, is shifted in the horizontal direction toward the cuvette 1 which is in the controlled position and projecting upward to some extent by the positioning unit 4, the cuvette 1 is stably held in a predetermined position and transported without being rotated.

If the cuvette 1 is supplied, for example, with corners 22 (shown in FIG. 2) of the top rectangular or square portion 17 being in contact with the inner surfaces of the upper gripping arms 23, 23 (that is, with lateral surfaces of the rectangular or square portion 17 not being parallel to the inner surfaces of the upper gripping arms 23, 23), horizontal shift of the upper gripping arms 23, 23 allows the corners 22 to abut against the tips of the upper gripping arms 23, 23 causing the upper gripping arms 23, 23 to be farther spaced apart, the upper gripping arms 23, 23 resisting the resilient force of the tensile coiled spring 26.

Here, since the upper gripping arms 23, 23, which are spaced far apart, hold the cuvette 1 by the corners 22 with a small contacting area, the cuvette 1 is in an unstable condition and can be easily rotated.

The cuvette 1 inevitably rotates until the inner surfaces of the upper gripping arms 23, 23 become parallel to the lateral surfaces of the top rectangular or square portion 17 of the cuvette 1 to render a stable condition under which the cuvette 1 is held by the top rectangular or square portion 17 between the upper gripping arms 23, 23.

Thus, the first cuvette-transporting apparatus 100 can force the cuvette 1 to rotate to the predetermined position and can stably hold the cuvette 1.

The cuvette 1, held by the first cuvette transporting apparatus 100, is supplied with a liquid specimen and a reagent by liquid-supplying units (not shown) in the course of transportation to a measuring unit (not shown). After completion of transportation to the measuring apparatus, the cuvette 1 containing the liquid and the reagent is accepted into an acceptor of the measuring unit at the predetermined position. Then, the measuring unit irradiates a measuring beam of light orthogonally to one of four sides of the lower rectangular portion 19 to measure transmitted light and/or scattered light which are emitted from the other sides of the lower rectangular portion 19, thereby analyzing various properties of the liquid.

In accordance with the present invention, the cuvette is externally provided with the rectangular or square portion so as to enable the cuvette to be held in a stable position and transported to the measuring unit without being rotated.

Further, in accordance with the present invention, the cuvette-transporting apparatus includes the linearly extending upper gripping arms and the internally curved lower gripping arms. The upper gripping arms hold the rectangular or square portion of the cuvette, whereby the cuvette is maintained in the predetermined position without being rotated. The lower gripping arms hold the cylindrical portion of the cuvette, rendering it difficult for the cuvette to slip down.

Even if the cuvette is not supplied in the predetermined position, the upper gripping arms enable the cuvette to be held in the predetermined position.

Thus, the cuvette can be transported maintaining the predetermined position.

Moreover, in accordance with the present invention, the cuvette-transporting apparatus includes a position-controlling devices for controlling the position of the cuvette while loose-fittingly holding the cuvette. In slide contact with the position-controlling devices, the cuvette is kept stable with the rectangular or square portion of the cuvette abutting against the position-controlling devices.

Accordingly, the cuvette always maintains its predetermined position.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A cuvette comprising:

a top portion including four side portions, the four side portions including two pairs of parallel side portions, and a circular flange portion beneath and extending outward from the four side portions;

a cylindrical central portion extending from the top portion; and a base portion, extending from the cylindrical central portion, including four side portions, each side portion being respectively parallel to at least one of the four side portions of the top portion.

2. The cuvette of claim 1, further including a cylindrical portion inside the cuvette.

3. The cuvette of claim 1, wherein the four side portions of the top portion are equal in length, thereby forming a square portion.

4. The cuvette of claim 1, wherein one pair of side portions of the top portion are of a first length and the other pair of side portions of the top portion are of a second length, different from the first length, thereby forming a rectangular portion.

5. The cuvette of claim 1, wherein the cylindrical central portion includes four tapered portions, each tapering the cylindrical central portion inwardly to meet one of the four side portions of the base portion.

6. The cuvette of claim 1, wherein the base portion is relatively narrower than the cylindrical central portion.

7. The cuvette of claim 6, wherein a bottom portion of the cylindrical central portion is tapered to connect to the relatively narrower base portion.

8. The cuvette of claim 1 wherein at least a portion of the cuvette is made light-pervious.

9. A cuvette comprising:

a top portion including four side portions, the four side portions including two pairs of parallel side portions;

a cylindrical central portion extending from the top portion; and a base portion, extending from the cylindrical central portion, including four side portions, each side portion being respectively parallel to at least one of the four side portions of the top portion, wherein a position of the cuvette is controlled by a position-controlling apparatus, the position-controlling apparatus including, cuvette-holding means for loose-fittingly holding the cuvette and for rotating the cuvette around a predetermined center; and position-controlling means for controlling the position of the cuvette by contacting at least one side portion of the pairs of parallel side portion during rotation by the cuvette-holdings means.

10. The cuvette of claim 9 wherein the cuvette is further transported by a cuvette transporting apparatus, the cuvette-transporting apparatus including, a pair of horizontally extending straight upper gripping arms for holding the top portion of the cuvette; and a pair of horizontally extending lower gripping arms, internally curved, for holding the cylindrical central portion of the cuvette.

position-controlling means for controlling the position of the cuvette by contacting at least one side portion of the two pairs of parallel [sides]side portions during rotation by the cuvette-holding means.

11. The cuvette of claim 10 wherein the upper gripping arms and lower gripping arms integrally open and close by a resilient force.

12. The cuvette of claim 9, wherein the position controlling means includes a first portion for contacting the cylindrical portion of the cuvette and a second portion for contacting and guiding the cuvette along one of the two pairs of parallel side portions.

13. The cuvette of claim 12, wherein the second portion of the position-controlling means further includes a tapered portion for initially contacting and guiding the cuvette.

* * * * *